United States Patent
Fox

(10) Patent No.: US 9,265,786 B1
(45) Date of Patent: Feb. 23, 2016

(54) METHOD FOR REDUCING PROTEIN MISFOLDING AND ACCUMULATION IN HUNTINGTON'S DISEASE CELLS

(71) Applicant: University of Wyoming, Laramie, WY (US)

(72) Inventor: Jonathan H. Fox, Laramie, WY (US)

(73) Assignee: University of Wyoming, Laramie, WY (US)

( * ) Notice: Subject to any disclaimer, the term of this patent is extended or adjusted under 35 U.S.C. 154(b) by 43 days.

(21) Appl. No.: 13/854,809

(22) Filed: Apr. 1, 2013

Related U.S. Application Data

(60) Provisional application No. 61/618,545, filed on Mar. 30, 2012.

(51) Int. Cl.
*A61K 48/00* (2006.01)
*A01N 63/00* (2006.01)
*A61K 31/711* (2006.01)

(52) U.S. Cl.
CPC .................................. *A61K 31/711* (2013.01)

(58) Field of Classification Search
CPC ...... C07K 14/47; C07K 16/18; C12Q 1/6883; A61K 31/711
USPC ....................................................... 514/44 R
See application file for complete search history.

(56) References Cited

U.S. PATENT DOCUMENTS

2010/0247496 A1* 9/2010 Leveillard et al. ......... 424/93.21

OTHER PUBLICATIONS

Calabrese et al 2007, Neurochem. Res. 32:757-773.*
Goswami et al 2006, BBRC 342:186-190.*
Akterin et al 2006,Cell Death and Differentiation 13:1454-1465.*
Zhou et al 2009, Brain Res. 1272:62-70.*

* cited by examiner

*Primary Examiner* — Scott Long
*Assistant Examiner* — Kelaginamane T Hiriyanna
(74) *Attorney, Agent, or Firm* — Samuel M. Freund; James M. Weatherly; Cochran Freund & Young LLC

(57) ABSTRACT

A method and virus for decreasing the levels of the disease-causing protein in Huntington's disease (mhtt) are described. Increased expression of human TXNDC10, and TXN1 in diseased cells decreases levels of toxic mhtt in cell models of disease. Genetically increasing the expression of the genes producing these proteins using viral vectors, or small molecule chemical activators of gene expression or stimulators of enzymatic activity, may be used to treat Huntington's disease in the asymptomatic carrier or affected human. Since other protein misfolding neurodegenerative diseases have many features in common with Huntington's disease, including the structure of the misfolded protein, the present method may be applicable to other protein misfolding neurodegenerative diseases.

4 Claims, 5 Drawing Sheets

METHOD FOR REDUCING PROTEIN MISFOLDING AND ACCUMULATION IN HUNTINGTON'S DISEASE CELLS

CROSS-REFERENCE TO RELATED APPLICATIONS

The present application claims the benefit of U.S. Provisional Patent Application No. 61/618,545 for "METHOD FOR REDUCING PROTEIN MISFOLDING IN CELLS" which was filed on Mar. 30, 2012, the entire content of which is hereby specifically incorporated by reference herein for all that it discloses and teaches.

STATEMENT REGARDING FEDERAL RIGHTS

This invention was made with government support under Grant Numbers 5P20RR015640-10 and 1R21NS072372-01 awarded by the U.S. National Institutes of Health. The government has certain rights in the invention.

FIELD OF THE INVENTION

The present invention relates generally to protein misfolding in cells and, more particularly, to methods for reducing levels of misfolded proteins in human Huntington's disease.

BACKGROUND

Protein misfolding neurodegenerative diseases are placing an increasing burden on society due to the aging population and lack of adequate treatment options. For example, Huntington's disease affects about 30,000 people in the United States, and has a slowly progressive course where patients can live with the condition for 10-20 years before death occurs. Huntington's disease is caused by a CAG repeat expansion within the huntingtin gene which results in a polyglutamine repeat expansion in huntingtin protein (htt). The mutant huntingtin protein (mhtt) misfolds and accumulates primarily in brain neurons where it mediates toxic effects resulting in neuronal dysfunction and loss, which ultimately results in loss of brain functions and disease manifestations such as involuntary movements, lack of coordination, loss of balance, memory loss, and dementia. Decreasing the level of mutant huntingin protein in the brain is predicted to be of therapeutic benefit in Huntington's disease; however, this has not been achieved in human Huntington's disease patients.

SUMMARY OF THE INVENTION

Embodiments of the present invention overcome the disadvantages and limitations of the prior art by providing a method for reducing protein misfolding in cells affected with Huntington's disease.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the method for reducing protein misfolding in cells, hereof includes: direct or indirect enzymatic modification of the disease-causing mhtt protein by increasing expression of specific thiol transferases in affected cells.

In another aspect of the present invention and in accordance with its objects and purposes, the method for reducing protein misfolding in cells hereof includes: promoting normal or improved cellular protein quality control by increasing expression of thiol transferases in affected cells effective for manipulating endoplasmic reticulum (ER) and cytosolic quality control.

Benefits and advantages of embodiments of the present invention include, but are not limited to, providing a therapeutic method for reducing levels of toxic mutant huntingin protein by increasing expression or activity of selected quality control proteins in cells of Huntington's disease gene positive patients or those manifesting the disease.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1:
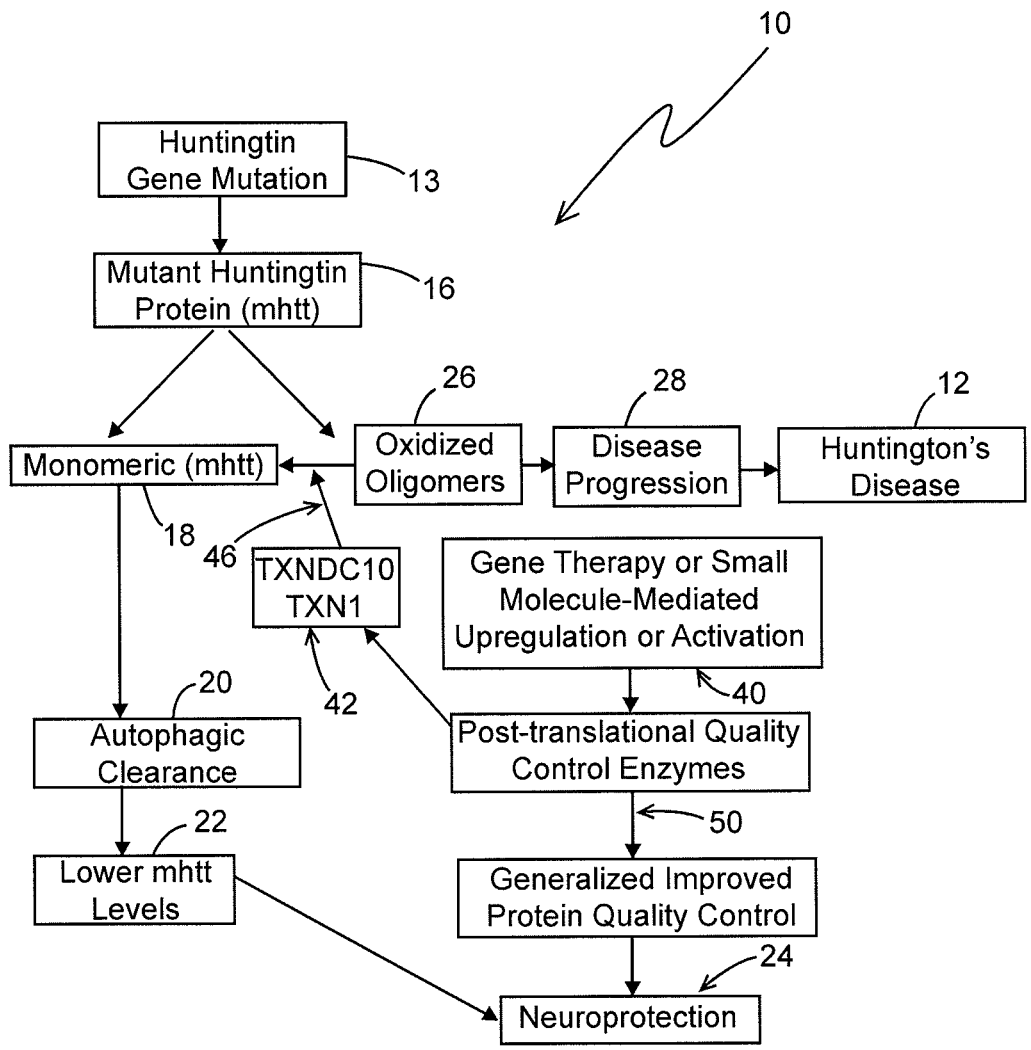
FIG. 1 is a schematic representation of methods for post-translational modification of Huntington's disease (HD) protein (mutant huntingtin protein (mhtt)) in accordance with embodiments of the present invention, illustrating improvement in diseased cell condition: (1) direct enzymatic modification of mutant huntingtin, or other disease-associated proteins; and/or (2) promoting normal or improved cellular protein quality control (only those disease pathways related to the present invention are illustrated).

Protein misfolding is involved in the pathogenesis of Huntington's disease (HD), prion diseases, amyotrophic lateral sclerosis, tauopathies, Parkinson's disease and Alzheimer's disease. In each of these diseases one or two key proteins misfolds, accumulates and causes cell dysfunction, death and eventually disease manifestation. Protein quality control is important for maintenance of health. The endoplasmic reticulum (ER) is a subcellular organelle that has a key role in protein quality control. Misfolded ER proteins are targeted for export to the cytoplasm where they are degraded in the proteasome in a process called endoplasmic-reticulum-associated degradation. Neurodegenerative processes can result in ER stress which impairs ER function and may result in a compensatory response called the unfolded protein response that involves upregulation of quality control pathways, mainly within the ER (See, e.g., M. L. Duennwald et al., "Impaired ERAD and ER stress are early and specific events in polyglutamine toxicity," Genes Dev. 22:3308-3319 (2008)). Quality control proteins also exist in other part of cells. For example, thioredoxins are cytosolic or mitochondrial proteins that maintain protein thiols in the correct oxidation status. Many quality control proteins are enzymes that modify protein structure.

Huntington's disease (HD) is caused by a CAG expansion within the huntingtin (htt) gene resulting in expression of a polyglutamine-expanded mutant huntingtin protein (mhtt) (See, e.g., The Huntington's Disease Collaborative Research Group, "HDCRG A novel gene containing a trinucleotide repeat that is expanded and unstable on Huntington's disease chromosomes," Cell 72:971-983 (1993)), which misfolds and accumulates in neurons eventually resulting in neurodegeneration and disease manifestations. In cell and mouse models of Huntington's disease, cysteine residues of mhtt have been reported to become oxidized and are involved in the formation and/or stabilization of oligomeric huntingtin species (See, J. H. Fox et al., "Cysteine oxidation within N-terminal mutant huntingtin promotes oligomerization and delays clearance of soluble protein," J. Biol. Chem. 286:18320-18330 (2011), the disclosure and teachings of which reference are hereby incorporated by reference herein.). It has also previously been reported that huntingtin oligomers are toxic and promote HD progression (See, e.g., I. Sanchez et al., "Pivotal role of oligomerization in expanded polyglutamine neurodegenerative disorders," Nature 421:373-379 (2003)).

Since other protein misfolding neurodegenerative diseases have many features in common with HD, including the structure of the misfolded proteins (R. Kayed et al., "Common structure of soluble amyloid oligomers implies common mechanism of parthenogenesis," Science 300:486-489 (2003)), the approaches identified hereinbelow may also be effective in the treatment of other protein misfolding diseases, such as: frontotemporal lobar dementia, amyotrophic lateral sclerosis and Parkinson's diseases.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto. Turning now to FIG. 1, a schematic representation of a method, 10, for post-translational modification of Huntington's disease (HD), 12, is illustrated. In the case of Huntington's disease, huntingtin gene mutation, 13, generates mutant huntingtin protein (mhtt), 16, which causes the disease, and which, if it remains in monomeric form, 18, is more efficiently cleared by a cell's autophagic processes, 20, leading to lower mhtt levels, 22, and slower disease progression, 24. Mutant huntingtin protein 16 may also generate oxidized oligomers which are cleared more slowly by the cell and accumulate, 26, leading to earlier disease onset and/or faster disease progression, 28, and 12.

In accordance with embodiments of the present invention and as will be explained in more detail hereinbelow, using gene therapy (See, e.g., Thomas B. Lentz et al., "Viral vectors for gene delivery to the central nervous system," Neurobiol. Dis. (2011)), or small molecules likely orally administered, post-translational quality control enzymes for Huntington's disease, 42, are generated or have enhanced activity. FIG. 1 further illustrates improvement in diseased cell condition by: (1) direct or indirect enzymatic modification of mutant huntingtin, 46, which leads to a decrease in oligomeric mhtt 26, ultimately leading to neuroprotection 24, as described hereinabove; and/or (2) promoting normal or improved cellular protein quality control, 50, leading to neuroprotection 24.

Figure 5:
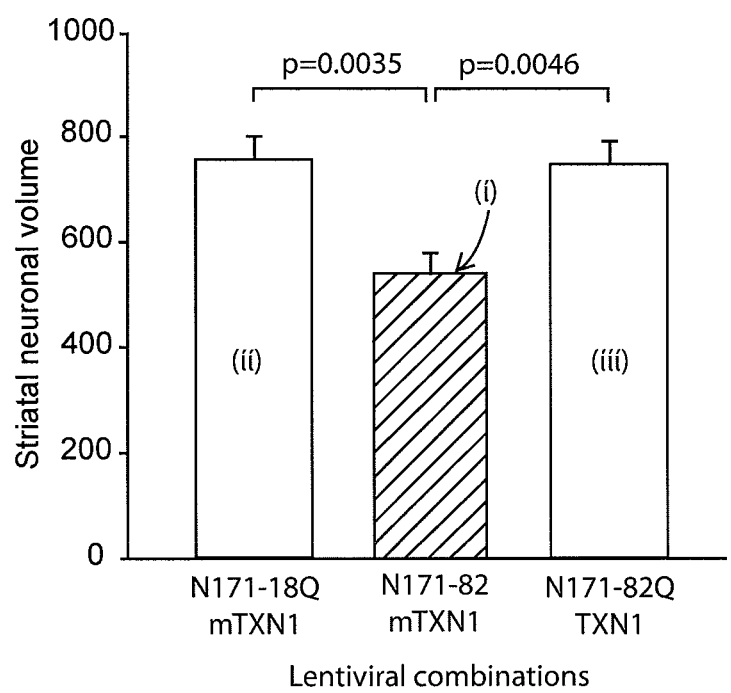
FIG. 5 shows the beneficial effect of TXN1 on B6/C3 F1 mice following co-transduction of lentiviruses expressing N171 huntingtin and either enzymatically active or inactive human TXN1.

In HD 12, oxidized oligomers 26 are cleared more slowly than monomeric huntingtin species 18 (J. Fox et al., supra). As will be illustrated in the EXAMPLES hereinbelow, increased expression of two quality control proteins 42 (thioredoxin 1 (TXN1) and TXNDC10 (Note that TXNDC10, also known as TMX3 (thioredoxin-related transmembrane protein 3), both proteins being well characterized proteins produced by brain cells (Thioredoxins, glutaredoxins, and peroxiredoxins—molecular mechanisms and health significance: from cofactors to antioxidants to redox signaling," by E. M. Hanschmann et al., Antioxid Redox Signal. 2013 Feb. 11; and "Identification and characterization of a novel thioredoxin-related transmembrane protein of the endoplasmic reticulum, J. Haugstetter et al., J. Biol. Chem. 2005 Mar. 4; 280(9):8371-80. Epub 2004 Dec. 28, respectively), have been found to decrease levels of mutant huntingtin in a cell culture HD model. Further, TXN1 has been found to provide protection in a mouse HD model as determined by quantitative neuropathology (FIG. 5).

Figure 2:
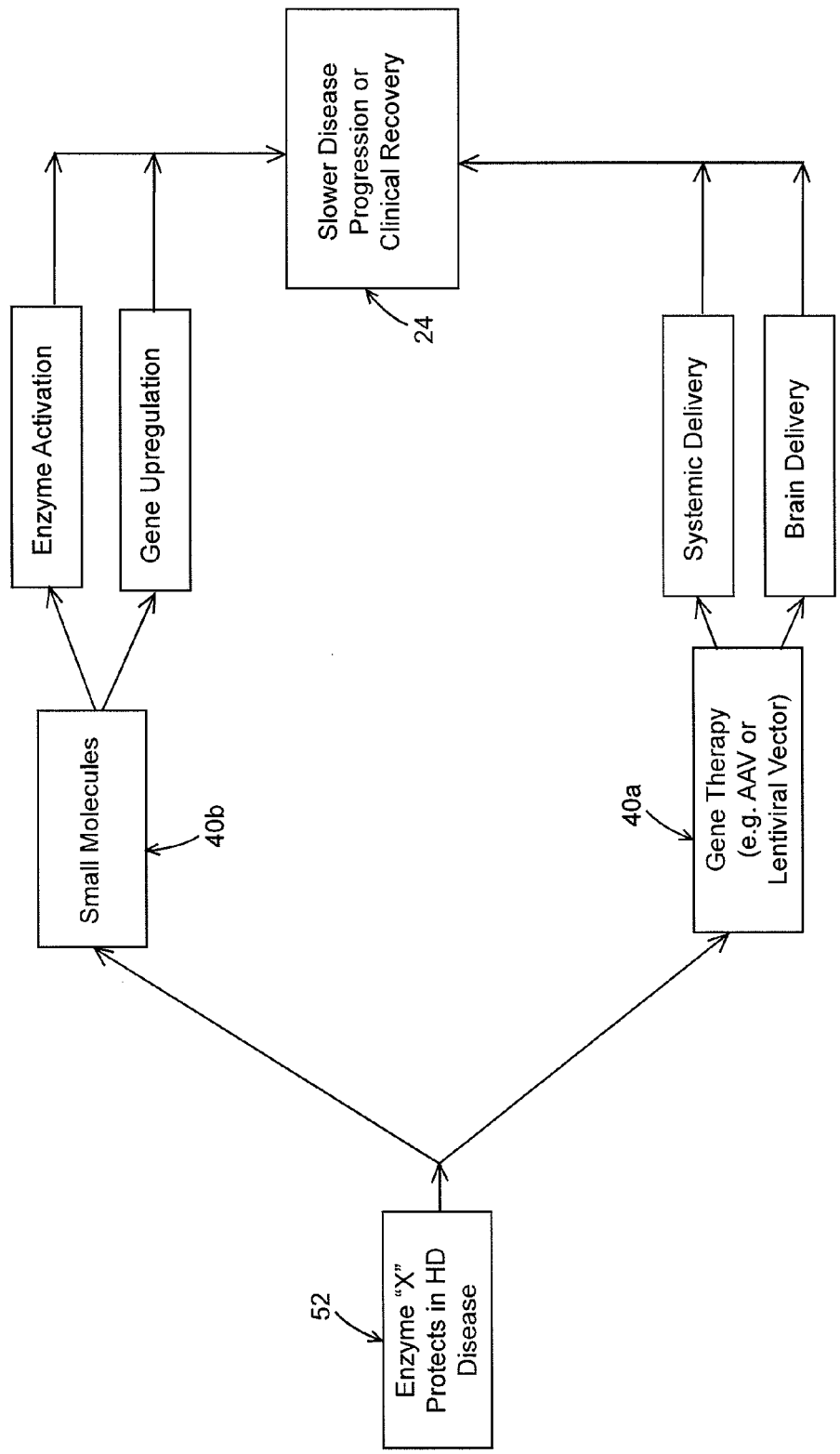
FIG. 2 is a schematic representation of the use of gene therapy and/or introduction of small molecules for increasing expression of the beneficial enzymes described in FIG. 1, hereof, or by direct or indirect enzymatic activation for modification of Huntington's disease (HD) proteins.

FIG. 2 is a schematic representation of the use of gene therapy, 40a, for example, use of the adeno-associated virus (AAV) or Lentivirus, as examples, and/or introduction of small molecules, 40b, for increasing the expression of the beneficial enzymes (Enzyme "X"), 52, described in FIG. 1, hereof, for modification of Huntington's disease (HD) 12 to achieve slower disease progression or even clinical improvement 24. In accordance with the teachings of embodiments of the present invention, direct or indirect enzymatic activation without increasing the amount of the protein is also expected to be of benefit (See, e.g., Julie A. Zorn et al., "Turning enzymes ON with small molecules," Nature Chem. Bio. 6, 179-188 (2010)).

Lentivirus is a genus of the Retroviridae family, and can deliver a significant amount of genetic information into the DNA of a host cell and, as such, is an efficient gene delivery vector. A common application is the use of a lentivirus to introduce a new gene into human cells. Lentiviral infection has advantages over other gene therapy methods including high-efficiency infection of dividing and non-dividing cells, long-term stable expression of a transgene, and low immunogenicity. Lentiviruses have been successfully used for transfection of diabetic mice with the gene encoding PDGF (platelet-derived growth factor), a therapy being considered for use in humans. The first clinical trial using a lentiviral vector was conducted in 2005 ("Regulatory Considerations for Novel Gene Therapy Products: A Review of the Process Leading to the First Clinical Lentiviral Vector," by Peter Manilla et al., Human Gene Therapy. January 2005, 16(1): 17-25. doi: 10.1089/hum.2005.16.17).

Figure 3:
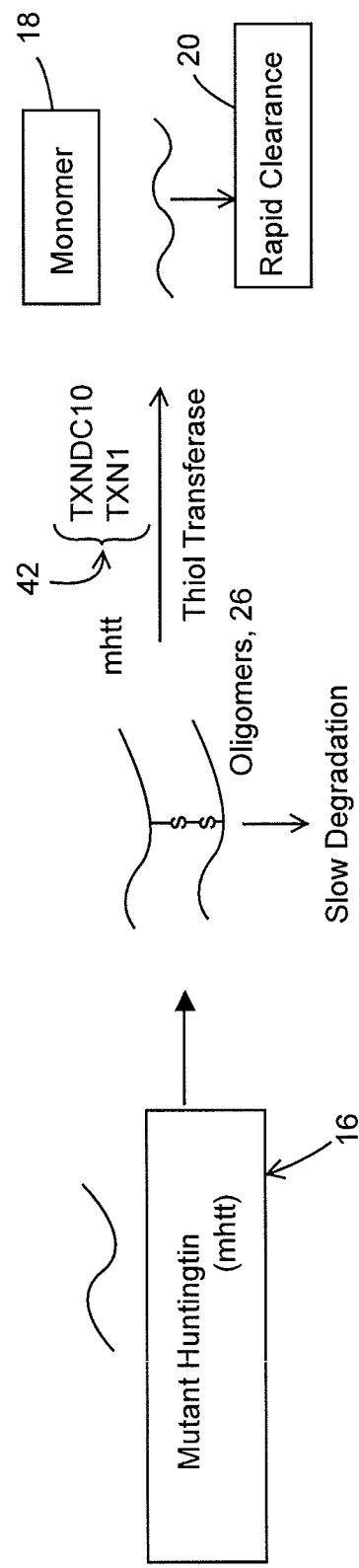
FIG. 3 is a schematic representation illustrating the promotion of cross-linking of mutant huntingtin protein from disulfide formation, and reversal of this process by specific thiol-transferases.

FIG. 3 illustrates promotion of cross-linking of mutant huntingtin by disulfide formation. As will be illustrated in the EXAMPLES hereinbelow, increased expression of specific quality control proteins decreases levels of the disease-causing proteins in HD (mhtt). Increased expression of human TXNDC10 and TXN1 decreases levels of toxic mutant huntingtin protein. Further, TXNDC10 and TXN1 chemically reduce or re-arrange disulfides in proteins as also illustrated in FIG. 3. TXNDC10 is an ER protein (See, e.g., J. Haugstetter et al., "Identification and characterization of a novel thioredoxin-related transmembrane protein of the endoplasmic reticulum," J. Biol. Chem. 280: 8371-8380 (2005).), while TXN1 is a cytoplasmic protein (See, e.g., C. Wu et al., "Thioredoxin 1-mediated post-translational modifications: reduction, transnitrosylation, denitrosylation, and related proteomics methodologies," Antioxid. Redox Signal 15:2565-2604 (2011).).

As illustrated in FIG. 2 hereof, genetic increase in expression may be achieved by use of viral vectors that could be delivered to the brain either by peripheral delivery or direct administration thereto, but once in the brain, they would express the therapeutic protein. An example of a viral system that could be used would be the adeno-associated viral (AAV) vector (See, e.g., Thomas B. Lenz et al., supra.), or the Lentivirus vector (See, e.g., Peter Manilla et al., supra). Also as shown in FIG. 2 hereof, small molecules may also be identified that increase levels of these proteins in cells (gene upregulators) or activate enzymatic activities. These might be delivered orally and cross the blood-brain barrier to achieve their desired effect. As illustrated in FIG. 1 hereof, the mechanism of decreased mhtt mediated by these gene products may be through enzyme mediated post-translational modification of the target protein (mhtt), or through indirect effects mediated via promotion of quality control pathways.

Having generally described embodiments of the invention, the following EXAMPLES provide additional details.

Example 1

The expression of forms of mhtt in cells that cannot form these oligomers has been shown to lead to a more rapid degradation and clearance of mhtt by an autophagy degradation pathway (Fox et al., supra), and gene products (enzymes) have therefore been sought that can convert oligomeric to monomeric protein. Embodiments of the present invention include therapeutic manipulation of thiol transferases and related enzymes to promote clearance of mhtt in HD. A genetic screen in cultured cells to identify thioltransferase enzymes that can decrease levels of mutant huntingtin protein identified two proteins: human thioredoxin 1 (TXN1) and human TXNDC10. A more rigorous secondary screen confirmed the findings from the initial screen. Genes encoding TXN1 and TXNDC10 were mutated such that enzymatically inactive (TXN1 and TXNDC10) proteins were expressed as controls leading to the demonstration that both TXN1 and TXNDC10 decrease mutant huntingtin protein levels in cells.

Figure 4A:
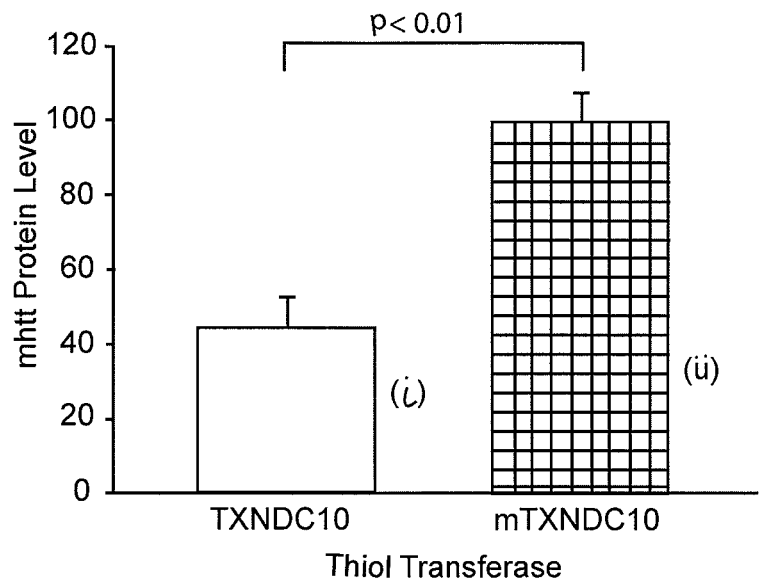
FIG. 4 shows the decrease in levels of mutant huntingin (N171-40Q) in cultured cells when active forms of TXNDC10 (bar (i) of FIG. 4A) and TXN1 (bar (i) of FIG. 4B) encoding plasmids were co-expressed with N171-40Q mutant huntingtin in COS cells, over those for the co-expression of the inactive forms thereof (bars (ii) of FIGS. 4A and 4B, respectively).
Figure 4B:
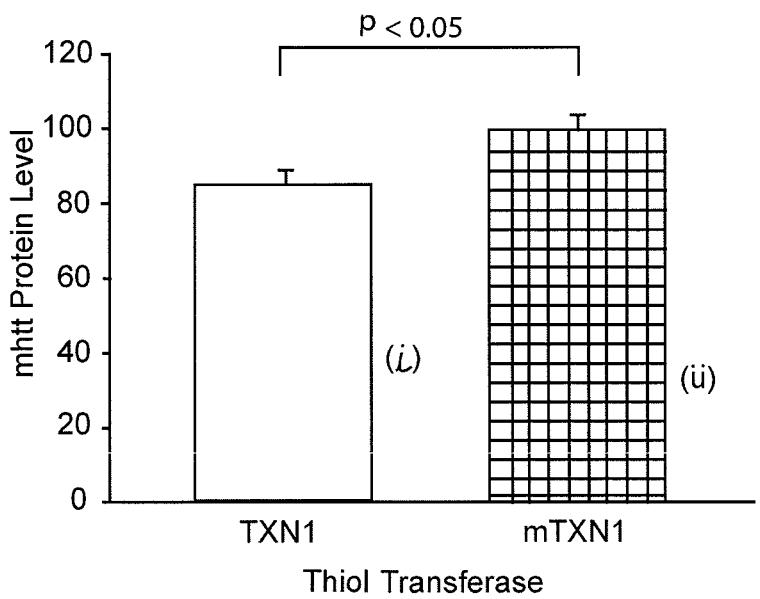

FIG. 4 shows the statistically significant (p) decrease in levels of mutant huntingin (N171-40Q), where Q is the single letter code for glutamine, in cultured cells when active forms of TXNDC10 (bar (i) of FIG. 4A) and TXN1 (bar (i) of FIG. 4B) encoding plasmids were co-expressed with N171-40Q mutant huntingtin in COS cells, over those for the co-expression of the inactive forms thereof (bars (ii) of FIGS. 4A and 4B, respectively). Enzymatically inactive proteins are produced by transfecting cells with DNA plasmids made by point mutagenesis of the DNA encoding one or more active site residues of the protein such that an inactive form of the protein will be encoded.

An initial screening of thiol reductase enzymes was performed in COS1 cells (maintained under standard conditions) co-transfected with plasmids encoding N171-40Q huntingtin and human thiol reductase enzymes or control plasmids. After two days, transfected cells were lysed, cell extracts were quantified for protein levels, then reducing Western blot analysis was used to measure total soluble N171-40Q huntingtin. Thiol transferases that decreased total soluble N171-40Q huntingtin levels were re-tested in a second, more rigorous assay. This second validation for confirming activity was obtained by generating active-site cysteine mutant versions of the 'hit' thiol transferases that lack enzymatic activity that were then used as negative controls in the experiments. (Enzymatically inactive versions of hits were made by mutation of active-site cysteine residues to alanine using the QuikChange site-directed mutagenesis kit (Stratagene)).

In the secondary assay, experiments were performed using plasmids encoding the active and inactive version of the 'hit' to determine if the active version of the protein decreased mhtt levels compared to the inactive version. Confirmed 'hit (s)' were subcloned into lentiviral expression plasmids to enable comparisons of the effect of injection of active 'hit' versus inactive 'hit' on outcomes in lentiviral HD mouse model (by co-viral injection).

Example 2

To extend the findings from cell culture experiments described in EXAMPLE 1 to mouse experiments TXN1 and mutant TXN1 DNA inserts were subcloned into a lentiviral four plasmid expression system. This was used to generate lentivirus in 293T cells. Virus was quantified by p24 ELISA. Viruses expressing N171 huntingtin fragments and either active or inactive TXN1 were co-injected into striata of 8-week old B6/C3H F1 female mice using stereotaxic surgery. Group 1=N171-18Q huntingtin+mutant TXN1; group 2=N171-82Q huntingtin+mutant TXN1; group 3=N171-82Q huntingtin+active TXN1. Four ng p24 of each virus were used per injection. The mice were sacrificed 8 weeks later and perfused with fixative for neuropathology analysis. Brain sections were fluorescently stained for huntingtin protein and Nissl substance. Images were captured using a confocal microscope. A stereologic approach called the nucleator was used to quantify neuronal cell body volumes in the region of the injection site. Decreased neuronal cell body volume is considered an indicator of neurodegeneration. As can be observed FIG. 5, N171-82Q (+inactive TXN1) expression (bar i) resulted in significantly smaller neuronal cell body volume than N171-18Q (+inactive TXN1) (bar ii) showing that mhtt (N171-82Q) decreases neuronal cell body volume compared to the equivalent normal fragment of huntingtin (N171-18Q). Further, mice injected with N171-82Q and active TXN1 expressing lentivirus (bar iii) had significantly larger neuronal cell body volumes compared to the control group showing that TXN1 rescues the degeneration caused by mhtt.

All DNA plasmids encoding the thiol transferase proteins were purchased from Qiagen (Life Technologies Corporation) as the QIAgenes expression construct system for mammalian cells. The principal features of the backbone plasmids are a cytomegalovirus (CMV) enhancer and chicken beta-actin hybrid promoter, synthesized and codon optimized human gene sequence, C-terminal histidine tag, two stop codons and then a 3-prime siRNA target sequence. (http://www.giagen.com/Products/QIAgenesExpressionKits-InsectMammalia.aspx?ShowInfo=1.) The N171 expression plasmids are widely available.

The lentiviral system is a four plasmid system, obtained as follows:

Plasmid 1: CMVdeltaR8.92 is the packaging plasmid (Lentiviral-mediated delivery of mutant huntingtin in the striatum of rats induces a selective neuropathology modulated by polyglutamine repeat size, huntingtin expression levels, and protein length, L. P. de Almeida et al. J. Neurosci. 2002 May 1; 22(9):3473-83);

Plasmid 2: pRSV Rev is another packaging plasmid. (de Almeida et al., supra; and http://www.addgene.org/12253/ (Peter Manilla et al., supra);

Plasmid 3: pMD.G expresses the envelope element VSV-G. (de Almeida et al., supra, and "In vivo gene delivery and stable transduction of nondividing cells by a lentiviral vector," L. Naldini et al., Science 1996 Apr. 12; 272(5259):263-7); and Plasmid 4: SIN-W-PGK plasmid contained the gene of interest being expressed (N171-82Q huntingtin, TXN1, TXNDC10) (L. P. Alameida et al.).

Viral particles were generated by co-transfection of all four plasmids into 293T cells from which virus is naturally released by cells into the medium and purified therefrom by centrifugation.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for controlling Huntington's disease in a human comprising increasing the expression of human thiol transferase chosen from TXN1 and TXNDC10 in the brain cells of said human effective for decreasing mutant huntingtin protein therein.

2. The method of claim 1, further comprising the step of orally administering a gene upregulator or activator for the human thiol transferase to said human.

3. The method of claim 1, further comprising the step of inducing expression of the thiol transferase in the cells of said human using a viral vector.

4. The method of claim 3, wherein the viral vector comprises lentivirus.

* * * * *